(12) United States Patent
Nishino et al.

(10) Patent No.: US 8,133,999 B2
(45) Date of Patent: Mar. 13, 2012

(54) PROCESS FOR PREPARATION OF 6, 7-BIS(2-METHOXYETHOXY) QUINAZOLIN-4-ONE

(75) Inventors: Shigeyoshi Nishino, Yamaguchi (JP); Kenji Hirotsu, Yamaguchi (JP); Hidetaka Shima, Yamaguchi (JP); Hiroyuki Oda, Yamaguchi (JP); Shinobu Suzuki, Yamaguchi (JP)

(73) Assignee: Ube Industries, Ltd., Ube-shi, Yamaguchi (JP)

( * ) Notice: Subject to any disclaimer, the term of this patent is extended or adjusted under 35 U.S.C. 154(b) by 0 days.

(21) Appl. No.: 12/484,632

(22) Filed: Jun. 15, 2009

(65) Prior Publication Data

US 2009/0253909 A1    Oct. 8, 2009

Related U.S. Application Data

(63) Continuation of application No. 10/565,981, filed as application No. PCT/JP2004/010965 on Jul. 30, 2004, now abandoned.

(30) Foreign Application Priority Data

Jul. 30, 2003   (JP) .................... 2003-282696

(51) Int. Cl.
    C07D 239/72    (2006.01)
(52) U.S. Cl. ..................................... 544/287
(58) Field of Classification Search ............ 544/287
    See application file for complete search history.

(56) References Cited

U.S. PATENT DOCUMENTS

| | | | |
|---|---|---|---|
| 3,119,824 | A | 1/1964 | Scarborough et al. |
| 4,096,144 | A | 6/1978 | Yamamoto et al. |
| 5,747,498 | A | 5/1998 | Schnur et al. |
| 2005/0080262 | A1 | 4/2005 | Nishino et al. |
| 2005/0124809 | A1 | 6/2005 | Nishino et al. |

FOREIGN PATENT DOCUMENTS

| | | |
|---|---|---|
| JP | 63-126867 A | 5/1988 |
| JP | 63-162670 A | 7/1988 |
| JP | 10-95776 A | 4/1998 |
| JP | 2002-293773 | 10/2002 |
| JP | 2002-293773 A | 10/2002 |
| WO | WO 03/000188 | 1/2003 |
| WO | WO 03/051849 A1 | 6/2003 |
| WO | WO 03/064339 A1 | 8/2003 |
| WO | WO 03/064399 | 8/2003 |

OTHER PUBLICATIONS

Stephen W. Wright, et al., Anilinoquinazoline Inhibitors of Fructose 1, 6-Bisphosphatase Bind at a Novel Allosteric Site: Synthesis, In Vitro Characterization, and X-ray Crystallography, Journal of Medicinal Chemistry, 2002, vol. 45, No. 18, pp. 3865 to 3877.
International Search Report, PCT/JP2004/010965 dated Aug. 31, 2004.
International Preliminary Report on Patentability and Written Opinion of the International Searching Authority, PCT/JP2004/010965, May 22, 2006.
Smith, Janice G., Organic Chemistry, New York: McGraw-Hill, 2006, pp. 817.
Bakalova, et al., Journal of Molecular Structure (Theochem), 710, 2004, pp. 230.
Mhaske, et al., Tetrahedron, 62, 2006, pp. 9791.

*Primary Examiner* — James O Wilson
*Assistant Examiner* — Douglas M Willis
(74) *Attorney, Agent, or Firm* — Nixon Peabody LLP; Jeffrey L. Costellia

(57) ABSTRACT

6,7-Bis(2-methoxyethoxy)quinazolin-4-one of formula (5) useful in synthesis of an anti-cancer drug can be prepared by a reaction of ethyl 2-amino-4,5-bis(2-methoxyethoxy)benzoate of formula (4) with an orthoformic acid in the presence of an ammonium acetate:

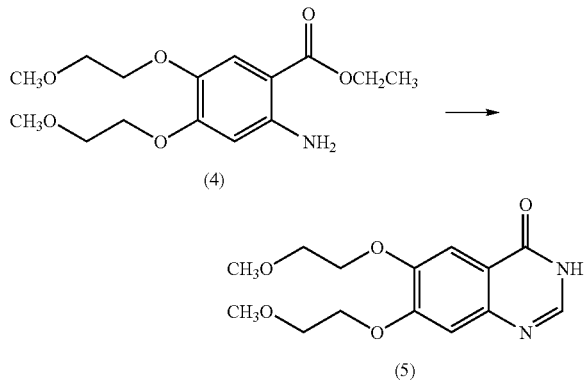

6 Claims, No Drawings

PROCESS FOR PREPARATION OF 6,7-BIS(2-METHOXYETHOXY)QUINAZOLIN-4-ONE

CROSS-REFERENCE TO RELATED APPLICATIONS

This application is a continuation of U.S. application Ser. No. 10/565,981, filed Jan. 26, 2006, which is a National Stage Entry of PCT/JP04/10965, filed Jul. 30, 2004, which claims priority to JP Application 2003-282696, filed Jul. 30, 2003.

BACKGROUND OF THE INVENTION (1) Field of the Invention

The present invention relates to a process for preparation of 6,7-bis(2-methoxyethoxy)quinazolin-4-one.

(2) Description of Related Art

U.S. Pat. No. 5,747,498 discloses 6,7-bis(2-methoxyethoxy)quinazolin-4-one as an intermediate in synthesis of 6,7-bis(2-methoxyethoxy)-4-(3-ethynylphenyl)aminoquinazoline hydrochloride, which can be used as an anticancer drug.

Japanese Patent Provisional Publication No. 2002-293773 discloses a process comprising a reaction of ethyl 2-amino-4,5-bis(2-methoxyethoxy)benzoate with ammonium formate to prepare 6,7-bis(2-methoxyethoxy)quinazolin-4-one. The publication reports that the yield of the reaction was 80.5%.

BRIEF SUMMARY OF THE INVENTION

A primary object of the present invention is to provide a process for preparing 6,7-bis(2-methoxyethoxy)quinazolin-4-one in a high yield from ethyl 2-amino-4,5-bis(2-methoxyethoxy)benzoate.

Another object of the invention is to provide an industrially advantageous process for preparing 6,7-bis(2-methoxyethoxy)quinazolin-4-one in a high yield using ethyl 3,4-dihydroxy-benzoate as a starting compound.

First, the present invention provides a process for preparation of 6,7-bis(2-methoxyethoxy)quinazolin-4-one, which comprises causing a reaction of ethyl 2-amino-4,5-bis(2-methoxyethoxy)benzoate with a formic acid compound in the presence of an ammonium carboxylate.

Second, the invention provides a process for preparation of 6,7-bis(2-meth-oxyethoxy)quinazolin-4-one, which comprises the steps in order of: causing a reaction of ethyl 4,5-bis(2-methoxyethoxy)-2-nitrobenzoate with hydrogen in the presence of a metallic catalyst to prepare ethyl 2-amino-4,5-bis(2-methoxyethoxy)benzoate; and causing a reaction of the ethyl 2-amino-4,5-bis(2-methoxyethoxy)benzoate with a formic acid compound in the presence of an ammonium carboxylate to prepare 6,7-bis(2-methoxyethoxy)quinazolin-4-one.

Third, the invention provides a process for preparation of 6,7-bis(2-methoxyethoxy)-quinazolin-4-one, which comprises the steps in order of. causing a reaction of ethyl 3,4-bis-(2-methoxyethoxy)benzoate with nitric acid in the presence of sulfuric acid to prepare ethyl 4,5-bis(2-methoxyethoxy)-2nitrobenzoate; causing a reaction of the ethyl 4,5-bis(2-methoxyethoxy)-2-nitrobenzoate with hydrogen in the presence of a metallic catalyst to prepare ethyl 2-amino-4,5-bis(2-methoxyethoxy)benzoate; and causing a reaction of the ethyl 2-amino-4,5-bis(2-methoxyethoxy)benzoate with a formic acid compound in the presence of an ammonium carboxylate to prepare 6,7-bis(2-methoxyethoxy)quinazolin-4-one.

Fourth, the invention provides a process for preparation of 6,7-bis(2-methoxyethoxy)-quinazolin-4-one, which comprises the steps in order of. causing a reaction of ethyl 3,4-dihydroxybenzoate with 2-chloroethyl methyl ether in an organic solvent in the presence of a base to prepare ethyl 3,4-bis(2-methoxyethoxy)benzoate; causing a reaction of the ethyl 3,4-bis(2-methoxyethoxy)benzoate with nitric acid in the presence of sulfuric acid to prepare ethyl 4,5-bis(2-methoxyethoxy)-2-nitrobenzoate causing a reaction of the ethyl 4,5-bis-(2-methoxyethoxy)-2-nitrobenzoate with hydrogen in the presence of a metallic catalyst to prepare ethyl 2-amino-4,5-bis(2-methoxyethoxy)benzoate; and causing a reaction of the ethyl 2-amino-4,5-bis(2-methoxyethoxy)benzoate with a formic acid compound in the presence of an ammonium carboxylate to prepare 6,7-bis(2-methoxyethoxy)quinazolin-4-one.

The formulas of the compounds involved in the process of starting from ethyl 3,4-dihydroxybenzoate and yielding 6,7-bis(2-methoxyethoxy)quinazolin-4-one are shown below.

Ethyl 3,4-dihydroxybenzoate is represented by the formula (1):

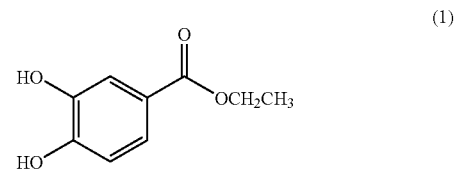

(1)

Ethyl 3,4-bis(2-methoxyethoxy)benzoate is represented by the formula (2):

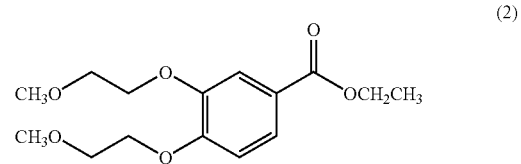

(2)

Ethyl 4,5-bis(2-methoxyethoxy)-2-nitrobenzoate is represented by the formula (3):

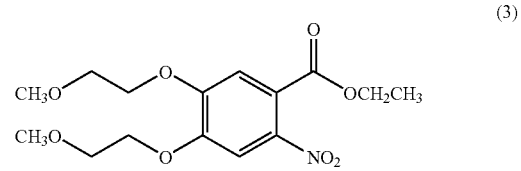

(3)

Ethyl 2-amino-4,5-bis(2-methoxyethoxy)benzoate is represented by the formula (4):

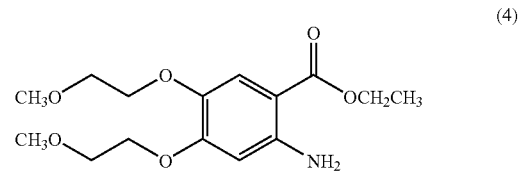

(4)

6,7-Bis(2-methoxyethoxy)quinazolin-4-one is represented by the formula (5):

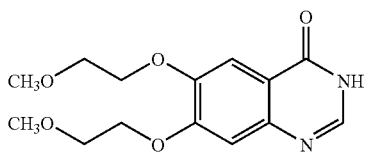

(5)

DETAILED DESCRIPTION OF THE INVENTION

The process for preparation of 6,7-bis(2-methoxyethoxy) quinazolin-4-one according to the present invention is described below by referring to the steps in order of:

causing a reaction of ethyl 3,4-dihydroxybenzoate with 2-chloroethyl methyl ether in an organic solvent in the presence of a base to prepare ethyl 3,4-bis(2-methoxyethoxy) benzoate (first step);

causing a reaction of the ethyl 3,4-bis(2-methoxyethoxy) benzoate with nitric acid in the presence of sulfuric acid to prepare ethyl 4,5-bis(2-methoxyethoxy)-2-nitrobenzoate (second step);

causing a reaction of the ethyl 4,5-bis(2-methoxyethoxy)-2-nitrobenzoate with hydrogen in the presence of a metallic catalyst to prepare ethyl 2-amino-4,5-bis(2-methoxyethoxy) benzoate (third step); and causing a reaction of the ethyl 2-amino-4,5-bis(2-methoxyethoxy)benzoate with a formic acid compound in the presence of an ammonium carboxylate to prepare 6,7-bis(2-methoxyethoxy)quinazolin-4-one (fourth step).

(A) First Step

In the first step, ethyl 3,4-dihydroxybenzoate reacts with 2-chloroethyl methyl ether in an organic solvent in the presence of a base to prepare ethyl 3,4-bis(2-methoxyethoxy) benzoate.

In the first step, the 2-chloroethyl methyl ether is used preferably in an amount of 1.0 to 20 moles, more preferably in an amount of 1.1 to 10 moles, and most preferably in an amount of 1.1 to 5.0 mole based on one mole of ethyl 3,4-dihydroxybenzoate.

Examples of the bases used in the first step include: alkali metal hydroxides such as sodium hydroxide, potassium hydroxide; alkali metal carbonates such as sodium carbonate and potassium carbonate; alkali metal hydrogencarbonates such as sodium hydrogencarbonate and potassium hydrogencarbonate; and alkali metal alkoxides such as sodium methoxide and potassium methoxide. The alkali metal hydroxides and the alkali metal carbonates are preferred. The alkali metal carbonates are more preferred. Most preferred is potassium carbonate. The base can be used alone or in combination.

The base is used preferably in an amount of 1.0 to 20 moles, more preferably in an amount of 1.1 to 10 moles, and most preferably in an amount of 1.1 to 5.0 moles based on one mole of ethyl 3,4-dihydroxybenzoate.

There are no specific limitations with respect to the organic solvent used in the first step, unless the organic solvent participates in the reaction. Examples of the organic solvents include: alcohols such as methanol, ethanol, isopropanol and t-butanol; ketones such as acetone, methyl ethyl ketone and methyl isobutyl ketone; amides such as N,N-dimethylformamide and N-methylpyrrolidone; ureas such as N,N'-dimethylimidazolidinone; sulfoxides such as dimethyl sulfoxide; nitriles such as acetonitrile and propionitrile; ethers such as diethyl ether, diisopropyl ether, tetrahydrofuran and dioxane; and aromatic hydrocarbons such as toluene and xylene. The ketones, nitriles and amides are preferred. The organic solvent can be used alone or in combination.

The amount of the organic solvent is adjusted in consideration of homogeneity of the reaction solution and stirring conditions. The organic solvent is used preferably in an amount of 1 to 100 g, and more preferably in an amount of 2 to 20 g based on 1 g of ethyl 3,4-dihydroxybenzoate.

The first step can be carried out, for example, by mixing ethyl 3,4-dihydroxybenzoate, 2-chloroethyl methyl ether. a base and an organic solvent under stirring in an inert gas atmosphere. The reaction temperature is preferably in the range of 20 to 200° C., and more preferably in the range of 40 to 120° C. There are no specific limitations with respect to the reaction pressure.

In the first step, ethyl 3,4-bis(2-methoxyethoxy)benzoate is obtained. After the reaction is complete, ethyl 3,4-bis(2-methoxyethoxy)benzoate can be isolated or purified for the second step. The isolation or purification can be conducted according to the conventional method such as filtration, concentration, distillation, recrystallization, crystallization, or column chromatography. Ethyl 3,4-bis(2-methoxyethoxy) benzoate can also be used in the second step without conducting isolation or purification. In the case that isolation or purification is not conducted, the solvent can be replaced in the second step.

(B) Second Step

In the second step, ethyl 3,4-bis(2-methoxyethoxy)benzoate reacts with nitric acid in the presence of sulfuric acid to prepare ethyl 4,5-bis(2-methoxyethoxy)-2-nitrobenzoate.

In the second step, nitric acid is used preferably in an amount of 1.0 to 50 moles, more preferably in an amount of 2.0 to 10 moles based on one mole of ethyl 3,4-bis(2-methoxyethoxy)benzoate. The nitric acid has a concentration preferably in the range of 40 to 90 wt. %, and more preferably in the range of 50 to 70 wt. %.

The second step is preferably carried out in the presence of a solvent. There are no specific limitations with respect to the solvent, unless the solvent participates in the reaction. Examples of the solvents include carboxylic acids such as formic acid, acetic acid, propionic acid and butyric acid. Acetic acid is preferred. The solvent can be used alone or in combination.

The amount of the solvent is adjusted in consideration of homogeneity of the reaction solution and stirring conditions. The solvent is used preferably in an amount of 1 to 50 g, and more preferably in an amount of 1.1 to 20 g based on 1 g of ethyl 3,4-bis(2-methoxyethoxy)benzoate.

The second step can be carried out, for example by mixing ethyl 3,4-bis-(2-methoxyethoxy)benzoate, nitric acid, sulfuric acid and a solvent under stirring in an atmosphere of an inert gas. The reaction temperature is preferably in the range of 20 to 90° C., more preferably in the range of 30 to 80° C., and most preferably in the range of 45 to 75° C. There are no specific limitations with respect to the reaction pressure.

In the second step, ethyl 4,5-bis(2-methoxyethoxy)-2-nitrobenzoate is obtained. After the reaction is complete, ethyl 4,5-bis(2-methoxyethoxy)-2-nitrobenzoate can be isolated or purified for the third step. The isolation or purification can be conducted according to the conventional method such as filtration, concentration, distillation, recrystallization, crystallization, or column chromatography. Ethyl 4,5-bis(2-methoxyethoxy)-2-nitrobenzoate can also be used in the third step without conducting isolation or purification. In the case that isolation or purification is not conducted, the solvent can be replaced in the third step.

(C) Third Step

In the third step, ethyl 4,5-bis(2-methoxyethoxy)-2-nitrobenzoate reacts with hydrogen in the presence of a metallic catalyst to prepare 2-amino-4,5-bis(2-methoxyethoxy)benzoate.

The metallic catalyst used in the third step can contain at least one metal atom selected from the group consisting of palladium, platinum and nickel. Examples of the metallic catalysts include palladium/carbon, palladium/barium sulfate, palladium hydroxide/carbon, platinum/carbon, platinum sulfide/carbon, palladium-platinum/carbon, platinum oxide and Raney nickel. Palladium/carbon, platinum/carbon, platinum sulfide/carbon and Raney nickel are preferred. The platinum/carbon catalyst is particularly preferred. The metallic catalyst can be used alone or in combination.

In the third step, the metallic catalyst is used preferably in an amount of 0.1 to 1,000 mg in terms of metal atom amount, and more preferably in an amount of 0.5 to 500 mg based on 1 g of ethyl 4,5-bis(2-methoxyethoxy)-2-nitrobenzoate. When the metallic catalyst comprises a metal carried on a carrier, the amount of the metal on the carrier preferably is in the range of 1 to 2.9 wt. % based on amount of the carrier.

In the third step, hydrogen is used preferably in an amount of 3 to 50 moles, and more preferably in an amount of 3 to 10 moles based on one mole of ethyl 4,5-bis(2-methoxyethoxy)-2-nitrobenzoate.

The reaction in the third step is preferably carried out in the presence of a solvent. There are no specific limitations with respect to the solvent, unless the solvent participates in the reaction, Examples of the solvents include, water; alcohols such as methanol, ethanol, isopropanol, n-butanol, and t-butanol; carboxylic esters such as methyl acetate, ethyl acetate, and methyl propionate; aromatic hydrocarbons such as benzene, toluene, xylene, and mesitylene; and ethers such as diethyl ether, tetrahydrofuran, and dioxane. The alcohols and carboxylic esters are preferred, and methanol and ethanol are more preferred. The solvent can be used alone or in combination.

The amount of the solvent is adjusted in consideration of homogeneity of the reaction solution and stirring conditions. The solvent is used preferably in an amount of 1 to 100 g, and more preferably in an amount of 2 to 30 g based on 1 g of ethyl 4,5-bis(2-methoxyethoxy)-2-nitrobenzoate.

The reaction of the third step can be carried out, for example by mixing ethyl 4,5-bis(2-methoxyethoxy)-2-nitrobenzoate, a metallic catalyst and a solvent under stirring in the presence of hydrogen gas (which can be diluted with an inert gas). The reaction temperature is preferably in the range of 0 to 300° C., and more preferably in the range of 20 to 200° C. The reaction pressure is preferably in the range of 0.1 to 10 MPa, and more preferably in the range of 0.1 to 2 MPa.

After the reaction is complete, the final product, i.e., ethyl 2-amino-4,5-bis(methoxyethoxy)benzoate, can be isolated or purified for the fourth step. The isolation or purification can be conducted according to the conventional method such as filtration, concentration, distillation, recrystallization, crystallization, or column chromatography. Ethyl 2-amino-4,5-bis(methoxyethoxy)benzoate can also be used in the fourth step without conducting the isolation or purification In the case that the isolation or purification is not conducted, the solvent can be replaced in the fourth step.

(D) Fourth Step

In the fourth step, ethyl 2-amino-4,5-bis(2-methoxyethoxy)benzoate reacts with a formic acid compound in the presence of an ammonium carboxylate to prepare 6,7-bis(2-methoxyethoxy)quinazolin-4-one.

Examples of the formic acid compounds include: formic acid; formic esters such as an ester of formic acid with a lower alcohol having 1 to 6 carbon atoms (e.g., methyl formate and ethyl formate); and orthoformic esters such as an ester of orthoformic acid with a lower alcohol having 1 to 6 carbon atoms (e.g., methyl orthoformate and ethyl orthoformate). Formic esters and orthoformic esters are preferred. More preferred are orthoformic esters. Most preferred are methyl orthoformate and ethyl orthoformate.

In the fourth step, the formic acid compound is used preferably in an amount of 1.0 to 30 moles, and more preferably in an amount of 1.1 to 10 moles based on one mole of ethyl 2-amino-4,5-bis(2-methoxyethoxy)benzoate.

In the fourth step, an ammonium carboxylate is used. Examples of the ammonium carboxylates include: ammonium aliphatic carboxylates such as an ammonium aliphatic carboxylate having 1 to 6 carbon atoms (e.g., ammonium formate, ammonium acetate, and ammonium propionate); and ammonium aromatic carboxylates such as an ammonium aromatic carboxylate having 7 to 12 carbon atoms (e.g., ammonium benzoate and ammonium dichlorobenzoate). Ammonium aliphatic carboxylates are preferred. More preferred are ammonium formate and ammonium acetate. Most preferred is ammonium acetate. The ammonium carboxylate can be used alone or in combination.

In the fourth step, the ammonium carboxylate is used preferably in an amount of 1.0 to 30 moles, and more preferably in an amount of 1.1 to 10 moles based on one mole of 2-amino-4,5-bis(2-methoxyethoxy)benzoate.

The reaction in the fourth step can be carried out in the presence of a solvent. The reaction can also be carried out without a solvent. There are no specific limitations with respect to the solvent, unless the solvent participates in the reaction. Examples of the solvents include alcohols such as methanol, ethanol, isopropanol, n-butanol, and t-butanol; amides such as N,N-dimethylformamide and N-methylpyrrolidone; ureas such as N,N'-dimethylimidazolidinone; sulfoxides such as dimethyl sulfoxide; aromatic hydrocarbons such as benzene, toluene, xylene, and mesitylene; halogenated hydrocarbons such as methylene chloride, chloroform, and dichloroethane; nitrites such as acetonitrile, and propionitrile; and ethers such as diethyl ether, tetrahydrofuran, and dioxane. The alcohols, amides and nitrites are preferred. More preferred are methanol, ethanol, N,N'-dimethylimidazolidinone and acetonitrile. The solvent can be used alone or in combination.

The amount of the solvent is adjusted in consideration of homogeneity of the reaction solution and stirring conditions. The solvent is used preferably in an amount of 0 to 50 g, more preferably in an amount of 0 to 20 g, and most preferably in an amount of 0 to 5 g based on 1 g of ethyl 2-amino-4,5-bis(2-methoxyethoxy)benzoate.

The reaction in the fourth step can be carried out, for example, by mixing an ammonium carboxylate, ethyl 2-amino-4,5-bis(2-methoxyethoxy)benzoate, a formic acid compound and a solvent under stirring in an inert gas atmosphere. The reaction temperature is preferably in the range of 40 to 200° C., and more preferably in the range of 50 to 150° C. There are no specific limitations with respect to the reaction pressure.

After the reaction is complete, the final product, i.e., 6,7-bis(2-methoxyethoxy)-quinazolin-4-one, can be isolated or purified. The isolation or purification can be conducted according to the conventional method such as filtration, concentration, distillation, recrystallization, crystallization, or column chromatography.

The present invention is further described by referring to the following examples.

EXAMPLES

Synthesis Example 1

(Synthesis of ethyl 3,4-bis(2-methoxyethoxy)benzoate)

In a 20 L-volume glass reaction vessel equipped with a stirrer, a thermometer and a reflux condenser, 1,300 g (7.14 moles) of ethyl 3,4-dihydroxybenzoate, 2,324 g (21.4 moles) of 2-chloroethyl methyl ether, 2,958 g (21.4 moles) of potassium carbonate and 6,500 mL of N,N-dimethylformamide were placed. The mixture was allowed to react with each other at 90 to 100° C. for 9 hours while stirring. After the reaction was complete, the reaction solution was cooled to room temperature. The reaction solution was then filtered, and washed with 6,500 mL of acetone. The filtrate was concentrated, 3,900 mL of ethyl acetate and 3,900 mL of a saturated aqueous sodium carbonate solution were added to the concentrate. The separated organic layer (ethyl acetate layer) was washed twice with 3,900 mL of a saturated aqueous sodium chloride solution to obtain a solution mixture containing ethyl 3,4-bis(2-methoxyethoxy)benzoate. The solution mixture was analyzed (according to an absolute quantitative method) by a high performance liquid chromatography. It was confirmed that 2,023 g of ethyl 3,4-bis(2-methoxyethoxy)-benzoate was produced (reaction yield: 95%). After 3,939 mL of acetic acid was added to the solution mixture, the mixture was concentrated under reduced pressure to distill ethyl acetate off. Thus, an acetic acid solution of ethyl 3,4-bis(2-methoxyethoxy)benzoate was obtained.

Synthesis Example 2

(Synthesis of ethyl 4,5-bis(2-methoxyethoxy)-2-nitrobenzoate)

In a 20 L-volume glass reaction vessel equipped with a stirrer, a thermometer and a reflux condenser, the acetic acid solution containing 2,023 g (6.78 moles) of ethyl 3,4-bis(2-methoxyethoxy)benzoate prepared in the Synthesis Example 1 was placed. To the solution, 318 g (3.18 moles) of concentrated sulfuric acid was gently added while stirring the solution at room temperature. The mixture was heated to 60 to 70° C. To the mixture, 1,857 g (20.34 moles) of 69 wt. % nitric acid was gently added while stirring the mixture. The resulting mixture was allowed to react for 2 hours while maintaining the temperature. After the reaction was complete, the reaction solution was cooled to room temperature. To the reaction solution, 5,200 mL of a 20 wt. % aqueous sodium chloride solution and 5,200 mL of toluene were added. The separated organic layer (toluene layer) was washed twice with 7,800 mL of a 1 mole per L aqueous sodium hydroxide solution, and further washed twice with 7,800 mL of a 20 wt. % aqueous sodium chloride solution. The organic layer was concentrated under reduced pressure to obtain 2,328 g of ethyl 4,5-bis(2-methoxyethoxy)-2-nitrobenzoate as an orange liquid (isolation yield: 100%).

Synthesis Example 3

(Synthesis of ethyl 2-amino-4,5-bis(2-methoxyethoxy)benzoate)

In a 20 L-volume glass reaction vessel equipped with a stirrer, a thermometer and a reflux condenser, 2,328 g (6.78 moles) of the ethyl 4,5-bis(2-methoxyethoxy)-2-nitrobenzoate prepared in the Synthesis Example 2, 2 wt. % platinum per 118 g of carbon (50 wt. % product, N.E. Chemcat Corporation, 6.0 mmoles in terms of platinum metallic atom) and 9,440 mL of methanol were placed. The mixture was allowed to react at 50 to 60° C. for 6 hours in an atmosphere of hydrogen while stirring. After the reaction was complete, the reaction solution was cooled to room temperature, and filtered. The filtrate was concentrated under reduced pressure to obtain 1,960 g of ethyl 2-amino-4,5-bis(2-methoxyethoxy) benzoate as an orange liquid (isolation yield: 92%).

Synthesis Example 4

(Synthesis of 6,7-bis(2-methoxyethoxy)quinazolin-4-one)

In a 20 L-volume glass reaction vessel equipped with a stirrer, a thermometer and a reflux condenser, 1,600 g (5.11 moles) of the ethyl 2-amino-4,5-bis(2-methoxyethoxy)benzoate prepared in the Synthesis Example 3, 1,626 g (15.3 moles) of methyl orthoformate, 1,181 g (15.3 moles) of ammonium acetate and 4,800 mL of methanol were placed. The mixture was allowed to react under refluxing conditions (60 to 70° C.) for 7 hours while stirring. After the reaction was complete, the reaction solution was cooled to 60° C. To the reaction solution, 4,800 mL of methanol was added. The mixture was stirred for 30 minutes while maintaining the temperature, cooled to 0 to 5° C., and further stirred for 1 hour. The resulting mixture was filtered to obtain 1,373 g of 6,7-bis(2-methoxyethoxy)quinazolin-4-one as white crystals (isolation yield: 91%).

The total yield based on ethyl 3,4-dihydroxybenzoate was 80%.

What is claimed is:

1. A process for preparation of 6,7-bis(2-methoxyethoxy) quinazolin-4-one, which comprises causing a reaction of ethyl 2-amino-4,5-bis(2-methoxyethoxy)benzoate with an orthoformic ester in the presence of ammonium acetate.

2. A process for preparation of 6,7-bis(2-methoxyethoxy) quinazolin-4-one, which comprises the steps in order of: causing a reaction of ethyl 4,5-bis(2-methoxyethoxy)-2-nitrobenzoate with hydrogen in the presence of a metallic catalyst to prepare ethyl 2-amino-4,5-bis(2-methoxyethoxy)benzoate; and causing a reaction of the ethyl 2-amino-4,5-bis(2-methoxyethoxy)benzoate with an orthoformic ester in the presence of ammonium acetate to prepare 6,7-bis(2-methoxyethoxy)quinazolin-4-one.

3. A process for preparation of 6,7-bis(2-methoxyethoxy) quinazolin-4-one, which comprises the steps in order of: causing a reaction of ethyl 3,4-bis(2-methoxy-ethoxy)benzoate with nitric acid in the presence of sulfuric acid to prepare ethyl 4,5-bis-(2-methoxyethoxy)-2-nitrobenzoate; causing a reaction of the ethyl 4,5-bis(2-methoxy-ethoxy)-2-nitrobenzoate with hydrogen in the presence of a metallic catalyst to prepare ethyl 2-amino-4,5-bis(2-methoxyethoxy) benzoate; and causing a reaction of the ethyl 2-amino-4,5-bis (2-methoxyethoxy)benzoate with an orthoformic ester in the presence of ammonium acetate to prepare 6,7-bis(2-methoxyethoxy)quinazolin-4-one.

4. A process for preparation of 6,7-bis(2-methoxyethoxy)-quinazolin-4-one, which comprises the steps in order of: causing a reaction of ethyl 3,4-dihydroxybenzoate with 2-chloroethyl methyl ether in an organic solvent in the presence of a base to prepare ethyl 3,4-bis(2-methoxyethoxy) benzoate; causing a reaction of the ethyl 3,4-bis(2-methoxy-ethoxy)benzoate with nitric acid in the presence of sulfuric acid to prepare ethyl 4,5-bis(2-methoxyethoxy)-2-nitrobenzoate; causing a reaction of the ethyl 4,5-bis-(2-methoxyethoxy)-2-nitrobenzoate with hydrogen in the presence of a metallic catalyst to prepare ethyl 2-amino-4,5-bis(2-methoxyethoxy)benzoate; and causing a reaction of the ethyl 2-amino-4,5-bis(2-methoxyethoxy)benzoate with an orthoformic ester in the presence of ammonium acetate to prepare 6,7-bis(2-methoxyethoxy)quinazolin-4-one.

5. The process according to claim 3 or 4, wherein the reaction of ethyl 3,4-bis(2-methoxyethoxy)benzoate with nitric acid in the presence of sulfuric acid is conducted at a temperature in the range of 45° C. to 75° C. to prepare ethyl 4,5-bis(2-methoxyethoxy)-2-nitrobenzoate.

6. The process according to claim 3 or 4, wherein the metallic catalyst comprises 1 to 2.9 wt. % of platinum on a carbon carrier.

* * * * *